(12) United States Patent
Gittleman

(10) Patent No.: US 6,726,477 B2
(45) Date of Patent: Apr. 27, 2004

(54) APPARATUS FOR IMPROVING THE REGISTRATION AND ARTICULATION OF DENTAL STONE REPLICAS

(76) Inventor: Neal B. Gittleman, 14 Greenway Plz., Houston, TX (US) 77098

( * ) Notice: Subject to any disclaimer, the term of this patent is extended or adjusted under 35 U.S.C. 154(b) by 101 days.

(21) Appl. No.: 10/210,630

(22) Filed: Jul. 31, 2002

(65) Prior Publication Data

US 2004/0023185 A1 Feb. 5, 2004

(51) Int. Cl.[7] ................................. A61C 11/00
(52) U.S. Cl. ..................... 433/34; 433/53; 433/60
(58) Field of Search ........................ 433/34, 53, 54, 433/58, 60, 37, 74, 49, 213

(56) References Cited

U.S. PATENT DOCUMENTS 5,466,152 A * 11/1995 Walter ...................... 433/60
5,769,634 A * 6/1998 Choi ......................... 433/64
6,551,102 B1 * 4/2003 Morales et al. ............ 433/60

FOREIGN PATENT DOCUMENTS

GB          2139092 A   * 11/1984   ........... A61C/11/00

* cited by examiner

*Primary Examiner*—Kevin Shaver
*Assistant Examiner*—Melba Bumgarner

(57) ABSTRACT

An aligning dental impression transfer method and apparatus is described in which the transfer of the bite registration in centric occlusion is accurately preserved from a triple tray impression to the positioning upon an articulator. At each stage of the casting of a working model the spatial relationship of existing dental structures are preserved.

12 Claims, 5 Drawing Sheets

APPARATUS FOR IMPROVING THE REGISTRATION AND ARTICULATION OF DENTAL STONE REPLICAS

BACKGROUND OF THE INVENTION

An innovative technique for producing a registered bite image of the teeth in centric occlusion begins with the molding of both the upper and lower teeth using a triple tray. The triple tray is formed from a rigid plastic or preferably metals frame having a lingual and buccal sidewall dam and a thin, porous mesh in the occlusal plane. This mesh is fine enough to allow good occlusion and still act as a support for a quick setting elastomeric compound of polysiloxane or other polymer that solidify to form a resilient rubber mold of the teeth in detail. Triple trays are available for the left or right dental arch and the anterior arch. The triple tray takes three simultaneous impressions of the upper and lower teeth, as well as the bite registration, thus earning its name. As an example, in the right arch, the "U" shaped frame is rigid enough to prevent the rubbery impression compound from expanding outward in subsequent casting procedures. This will prevent dimensional inaccuracies in the final restoration. An aluminum or steel frame has the necessary rigidity while occupying little space within the mouth. A convenient handle, preferably detachable, aids in the proper placement of the triple tray.

The triple tray with its embedded and solidified impressions is sent to the dental laboratory for further processing. A set of positive stone casts made from a quick setting plaster are formed within both the upper and lower negative impressions. Registering and attaching these positive stone casts is the subject of this invention. It is desirable that these stone casts are manipulated to mimic the variety of motions of the jaw to provide efficient and comfortable chewing. This is especially necessary when several missing teeth are being restored. The dental practitioner must craft the opposing surfaces while moving the stone casts from side to side and forward and backward matching the dynamic occlusal activity of the jaw. Cusps and fossae are sculpted where necessary to provide the crushing, grinding and cutting action of natural teeth. Often, the dental practitioner or laboratory artisan can improve upon the less than optimal dentition provided by inheritance. The upper and lower casts are held in an articulator in such a manner as to mimic the complex motion of the human jaw. The articulator of choice in this invention consists of a somewhat flexible hinged assembly having a radial opening and closing motion like that of the jaw. In addition the controlled flexing motion of the articulator arms allow the dental practitioner or artisan to manipulate the stone casts by hand. The articulator is provided with removable, adjustable frontal and rear stops.

The current techniques in sophisticated dental laboratories are reliant upon the knowledge and skill of the well trained dental technician to produce prosthetic crowns and bridges that match the opposing dentition. When working with separate casts of the upper and lower arch of the jaw, the technician can often attach the casts to an articulator by visual inspection with good accuracy. In some cases however, the technician must interpolate the desired occlusion. This may be the result of missing or poorly matching teeth. The use of the triple tray gives the technician a tool to replicate prosthetics that best meet the patient's own sense of his best bite pattern. In this manner the patient is most pleased with the results. However, if the technician should misalign the upper and lower casts by a few microns in cementing them to the jaws of the articulator, the patient will notice the misalignment in the resulting prosthesis.

If one or more teeth being restored are sectioned from the stone cast to allow for easier manipulation while building up the prosthesis, they must be accurately replaced among the other replicas of unaltered teeth in the stone cast. This is often done with alignment or registration pins that are easily slid in and out of matching receptacles formed in a separately cast stone base.

This invention offers refinements in the methods and apparatus by introducing a set pair of opposing articulator pin blocks with repositionable pins. The technician locates the optimal pin position within a block having an array of closely spaced holes. The pins are equipped with heads or a knurled region to hold firmly within the stone cast. The triple tray is first equipped with a confining dam to provide bases for the upper and lower impressions. The plaster slurry is fed into one side of the impression. A vibrating table having a jarring vertical motion, forces the thixotropic slurry to flow into each detail of the mold while driving any entrained bubbles to the top. The first impression block with the pins in place is positioned over the triple tray and locked and registered by means of projections on the dam mating with matching mounting holes in the block. After the plaster has set, the positive stone cast is carefully removed from triple tray impression and the confining dam. The stone cast can be sectioned with a thin saw blade down to the pin block. Each section can be removed and replace by sliding the pins out of and back into the block. The opposing positive stone cast is made using the same procedure by inverting the dam and triple tray assembly and filling the lower plaster recess with plaster slurry.

It is now possible to slide both the upper and lower block into the articulator. The articulator is equipped with an upper and lower frame with slide grooves for receiving the blocks in proper alignment. A detent means with a positive "snap" will tell the technician when the blocks are in place. Attracting embedded magnets in both the pin block and articulator jaws can provide good pin block positioning and retention. The articulator has an upper and lower arm attached to the upper and lower frame respectively. The upper and lower arms meet at a hinge that mimics the overall motion of the jaw. At least one of these arms has an elastically flexible element that will allow the two frames to move in lateral and anterior directions to mimic the complex motions of the jaws. When not being manipulated, the articulator frames return to an aligned resting position.

The apparatus of this invention consist of the following elements: A triple tray constructed of a sturdy metal frame and a thin porous membrane mounted on this frame in the occlusal plane known to the art.

A confining rubber dam with an upper and lower plaster casting recess that wraps around the periphery of the triple tray frame and locks into place.

An upper articulator block with a multitude of evenly spaced tapered through-holes, each plugged with a removable rubber plug. The articulator block is made from a transparent, rigid polymer. The plugs are made of a resilient polymer.

A plurality of tapered pins having a tapered base matching the tapered through-holes in the articulator blocks and having a knurled or otherwise machined head to hold the pin within hardened stone.

A lower articulator block and pin set fashioned like the upper block and pins.

Outline of the Steps

The dental technician needs to properly register the occlusal fit between the upper and lower stone casts of at least a section of the teeth. The problem in maintaining this registration as the upper and lower stone casts are attached to an articulator is the subject of this invention.

The dentist takes a triple tray impression of the upper and lower jaw with the teeth held shut in the normal bite position known as centric closure. A single quadrant, left or right or an anterior registration is captured. A full dental arch is also possible. The preferred impression material used is quick setting polymer paste, which sets to a rubbery solid.

Every detail of the dentition and surrounding soft tissue is captured. The triple tray is removed from the patient's mouth and sent to a lab. The excess rubber compound is trimmed from the surrounding areas of the triple tray, taking care not to disturb the areas of interest.

A prefabricated dam assembly having an upper and a lower pouring recess is fitted around the periphery of the triple tray. The fitting will be liquid tight, but will not distort the triple tray in a manner that would otherwise distort the restoration. This dam assembly has coined hinges that allow the assembly to be folded around the triple tray and locked into position. This confining dam has a partitioning shelf and a pair of upper and lower enclosing walls to form upper and lower recesses for the liquid casting slurry that will harden into a dimensionally accurate upper and lower stone models with mounting bases.

An articulator pin block is prepared with removable tapered pins to match the specific restoration areas. One or more replicated portions of the positive stone cast will be removably attached to the articulator block by means of these tapered pins. The articulator block is equipped with a multitude of equally spaced tapered holes, each sealed with a removable rubber plug. The plugs corresponding to the desired pin positions are punched out leaving an empty tapered hole for each desired pin placement.

The block has mounting and registration means to properly fix it to the top of the walls of the dam. The assembly is thinly coated with a mold release compound to aid in freeing the set stone model from the articulator block and surrounding dam.

A slurry of stone plaster is mixed and degassed according to the manufacturer's instructions.

The upper pouring recess of the dam and triple tray assembly is filled and bubbles are forced to the top of the recess with a tabletop, impact vibrator.

The prepared articulator block is inverted in the properly keyed location with the pins in place. The stone is allowed to harden. The positive stone cast of the upper rubber dam recess is left in place and the whole assemblage is turned upside down.

Now the lower articulator block with tapered pins inserted is prepared in the same manner as the upper block.

Plaster slurry is carefully ladled and vibrated into the triple tray lower impression and lower dam recess. The lower articulator block with its alignment pins in place is set and keyed into the plaster slurry. After hardening, the lower positive cast and the lower articulator block are removed from the lower triple tray impression and dam assembly.

The upper positive cast and articulator block are removed from the upper impression in the same manner as the lower cast and block.

Now the upper block with the attached positive cast is slipped into the matching groove in the upper articulator arm. The lower block is slipped into its matching groove on the lower articulator arm.

Centric occlusion is preserved since both the upper and lower stone casts were registered to the upper and lower articulator pin blocks during casting and the pin blocks were held in registration with the triple tray and dam assembly by keyed features.

A DETAILED DESCRIPTION OF THE DRAWINGS

Figure 1:
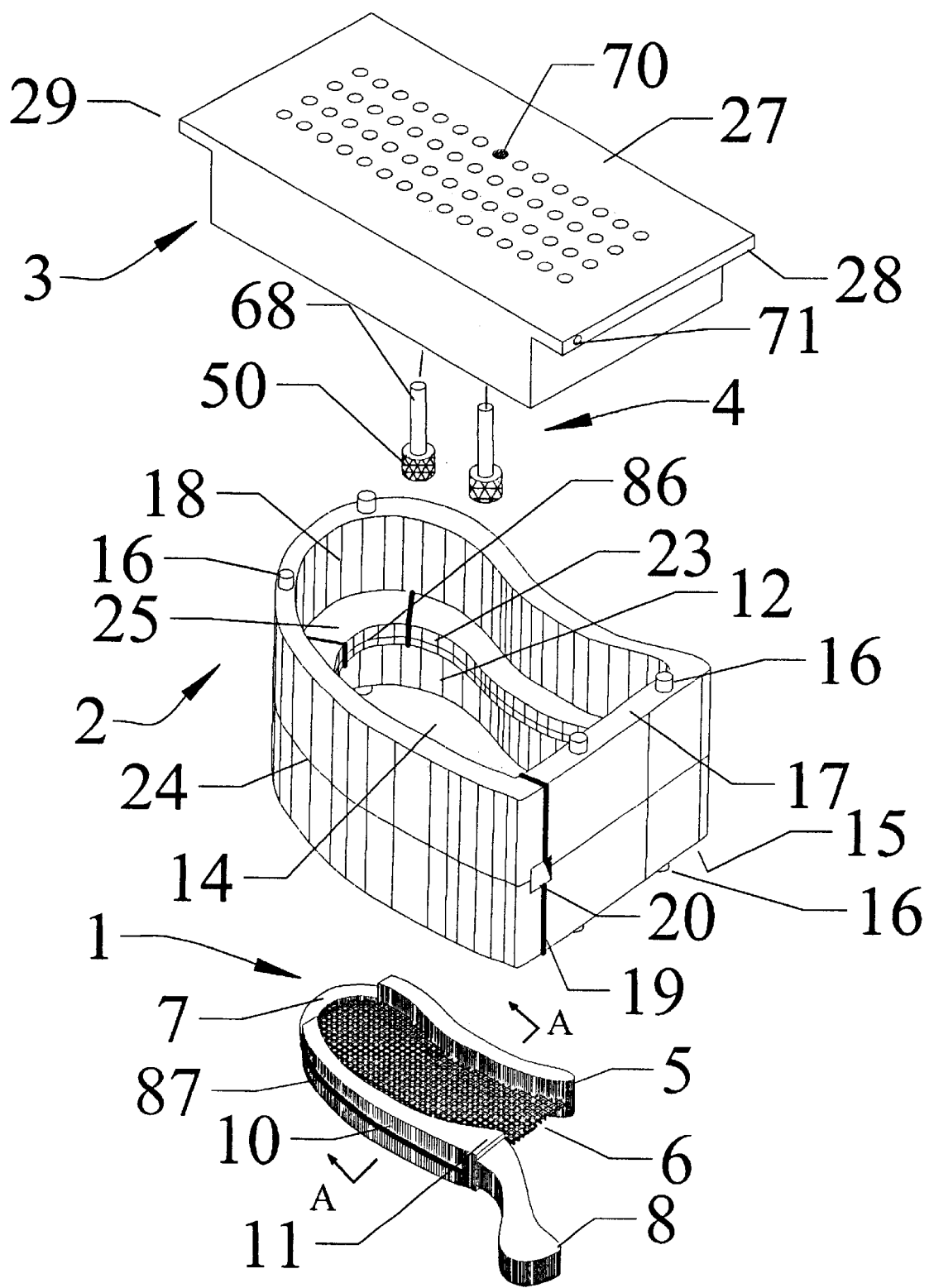
FIG. 1 is an exploded perspective view of the triple tray, plaster dam assembly, articulator pin block and alignment pins.

FIG. 1 details a triple tray 1 having a frame 11 with a buccal side 10, a transverse portion 7 and a lingual side 5. Mesh 6 is thin and flexible and offers minimal interference in the occusal plane during the taking of the simultaneous upper and lower impression. The frame is rigid to prevent distortion of the impression material. Handle 8 offers convenient placement and may be detachable. If the handle is maintained as an integral portion of the frame, the dam assembly 2 can accommodate the handle with opening 20 that forms a seal around the neck of the handle and prevent any liquid plaster from leaving the dam assembly. The dam assembly is shown with a parting seam 19 that allows the flexible dam material to be unwrapped from around the triple tray. Suitable closure means (not shown), such as a clasp, interlock or latch hold the parting seam closed and the dam in place around the triple tray. Though the confining dam is shown to be of a single piece construction, this invention is intended to encompass alternate embodiments, in which the dam is manufactured of two or more interlocking pieces conforming to the periphery of the triple tray frame.

Figure 2:
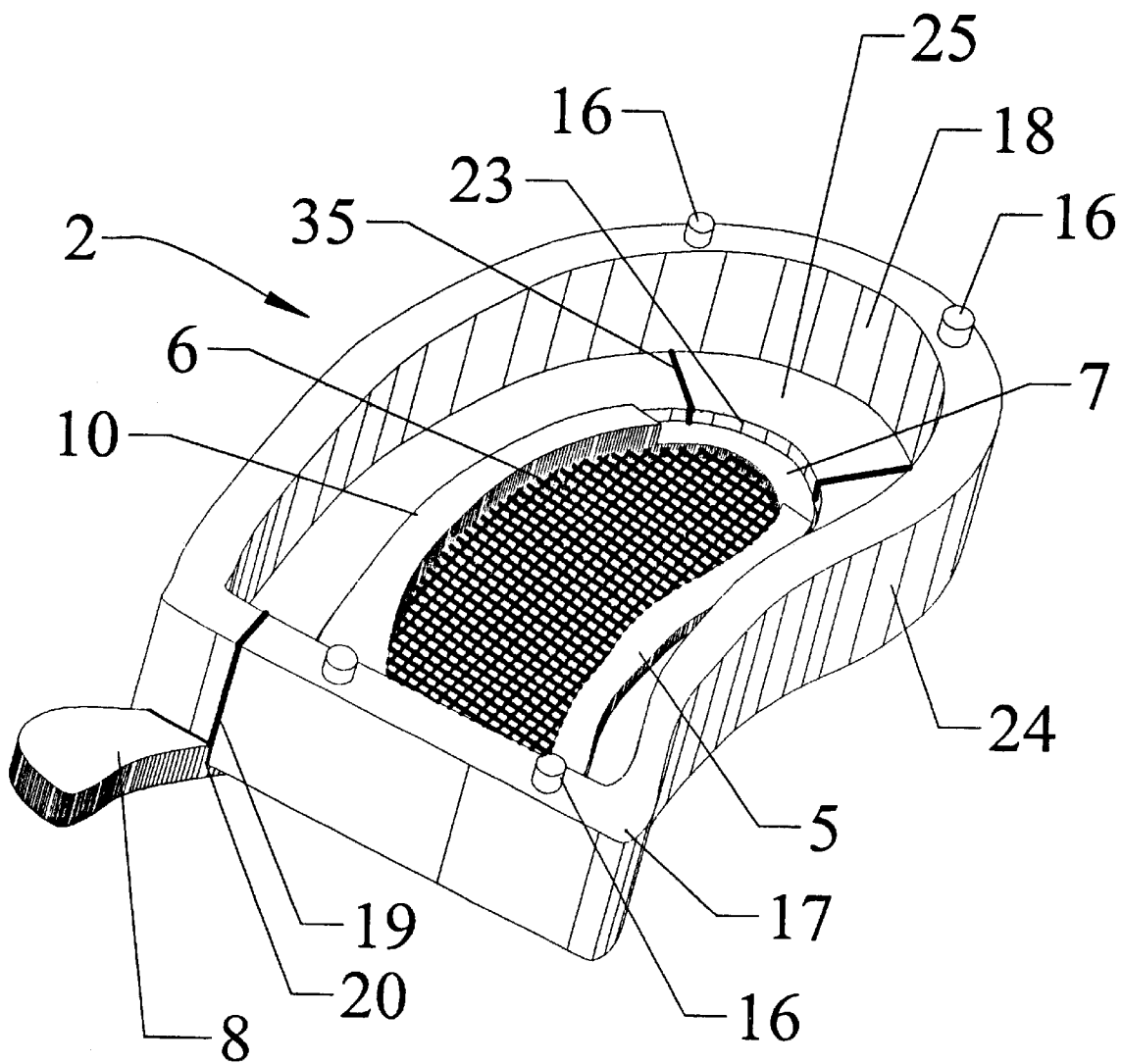
FIG. 2 is a perspective view of the top half of the plaster dam assembled around the triple tray.

The reusable plaster dam assembly is molded from a durable material to form an upper and a lower plaster dam recess. The dam assembly consists of an outer wall 24 and an inner wall 18. The internal space 14 has an upper chamber formed by surrounding inner wall 18 and an inner shelf 25. Surrounding inner wall 12 and the underside of inner shelf 25 forms the lower chamber. Inner shelf 25 has an inner surface 23 that fits closely about the outer peripheral surface of the triple tray in the manner shown in FIG. 2. Together triple tray 1 and barrier dam 2 form a casting cup for liquid plaster slurry. The upper chamber is cast and allowed to set, the assemblage inverted and then the lower chamber cast and set.

To aid in wrapping the dam around the triple tray, cuts 35 add flexibility, yet form a liquid tight seal when the dam assembly is secured. If necessary, sealing wax or grease can be applied to leaking joints in the dam and triple tray assembly after testing with water and drying with compressed air. Measuring the amount of water used to fill the recess can be used to approximate the amount of plaster mixture. In FIG. 1, the inner surface 23 can be equipped with an inwardly protruding lip 86 in the occlusal plane 86, which can project into a matching groove 87 in the periphery of the triple tray frame 11 to maintain parallel registration between the triple tray and the surrounding plaster dam. A protective stripping film or coating covers the groove 87 to allow easy removal of excess polymer from within the groove during the process of trimming the polymer from periphery of the triple tray. Alternately, a few well placed protrusions on the periphery of the triple tray frame can fit into matching recesses in the inner surface of shelf 23 to maintain parallel registration between the triple tray and the dam. A groove located in the inner wall of inner shelf 23 mating with the transitional portion 7 of the triple tray frame in combination with the closely held triple tray handle 8 in the confining dam access hole 20 will maintain parallel registration. FIG. 1 shows alignment stubs 16 in top surface 17 that correspond to matching holes in pin block 3. When the pin block is placed in position on the alignment stubs and seated against the top surface, it is maintained in a parallel and indexed position relative to the triple tray occlusal plane. In a similar fashion, a pin block will be seated against dam surface 15 on alignment stubs 16. Protruding ridges 28 and 29 on the pin block fit within matching grooves on the upper and lower jaws of the articulator. Dimple 71 has a matching snap projection within the articulator groove to confirm positive seating of the pin block. A representative plug 70 is shown in one of the pin block holes 26. In practice, all of the pin block holes will be plugged with removable elastic plugs. Only those holes selected for pin use will have a plug removed. The plugs prevent egress of plaster into holes and interference with the partition of the stone model from the pin block.

Pins 4 are shown with knurled head 50 and tapered shank 68. These pins are inserted within selected holes 26 in pin block 3 after resilient plugs 70 have been removed.

Figure 3:
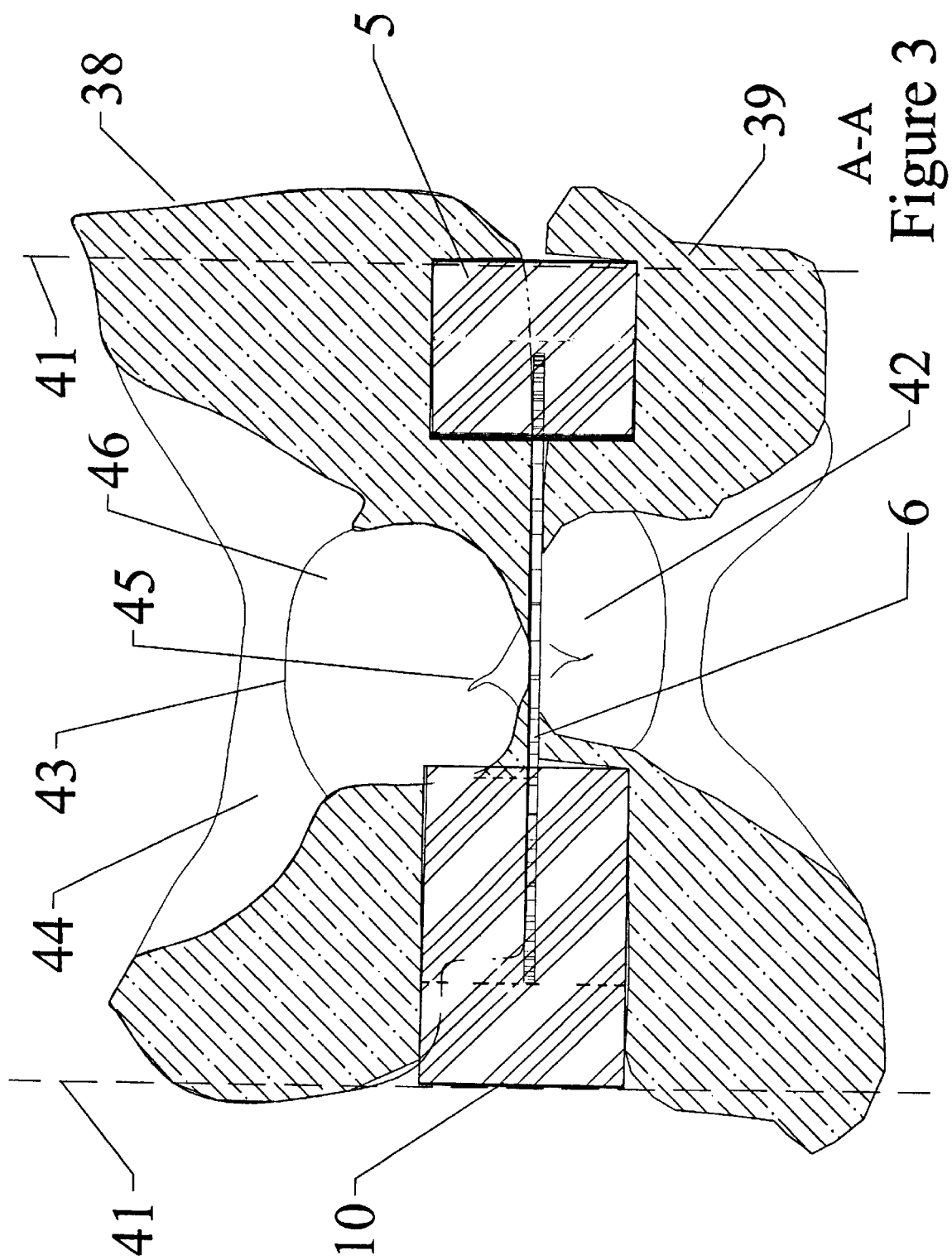
FIG. 3 is a sectioned view of the triple tray with impression molding compound.

FIG. 3 details a transverse sectional view of a typical triple tray with impression material attached. Buccal side 10 and lingual side 5 are shown surrounding and containing the thin flexible open mesh 6. Upper impression material 38 and lower impression material 39 are linked through the open mesh and hold negative impressions of the upper and lower dental arch. A negative image of an upper tooth 46, gum line 43, soft tissue 44 and occlusal surface features 45 are preserved in accurate detail. Impression of lower tooth 42 is in perfect registration with upper impression of tooth 46 in centric occlusion. Excess impression compound is trimmed with a scalpel from the outer perimeter of the triple tray frame along cut lines 41.

Figure 4:
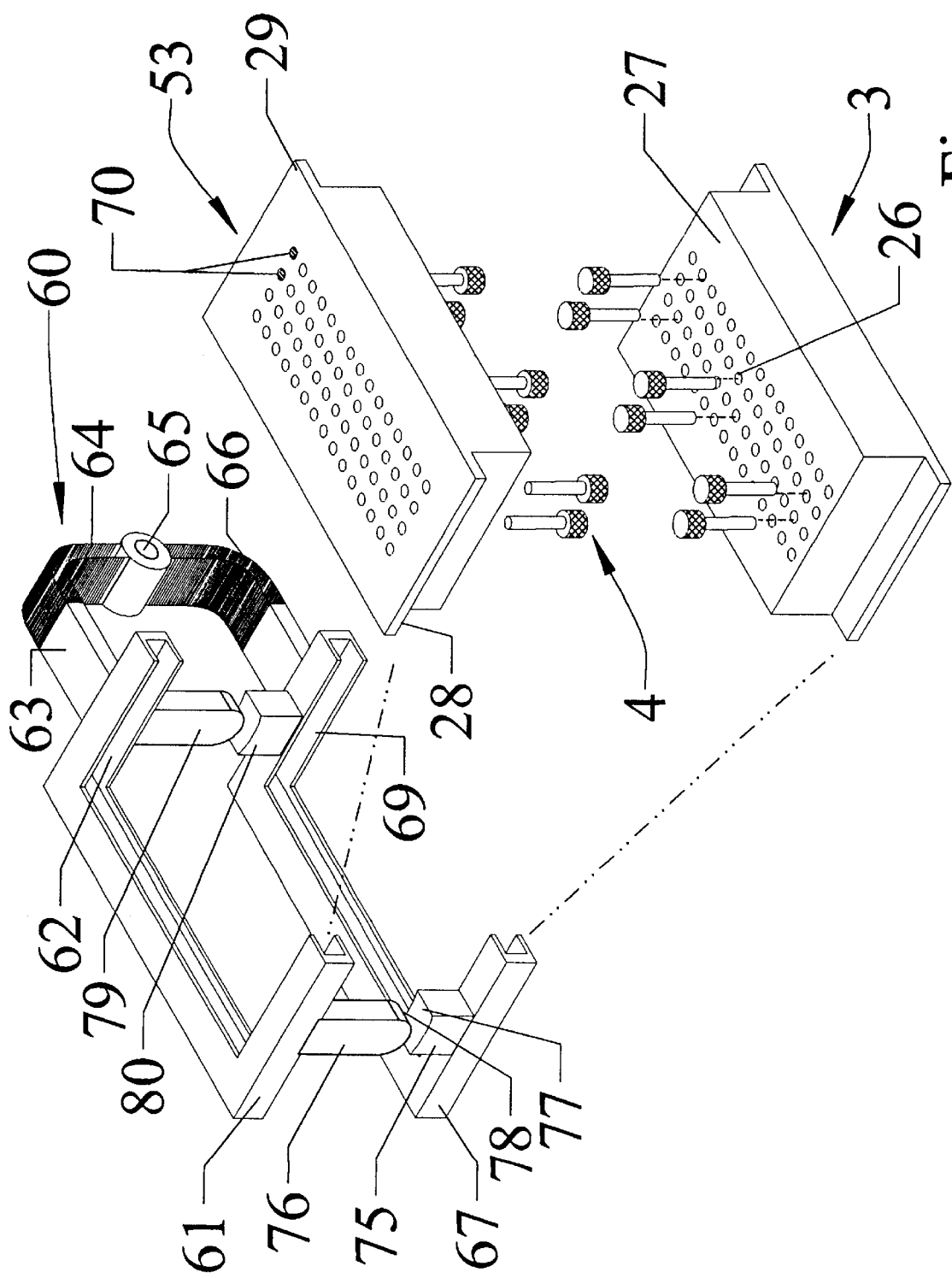
FIG. 4 is a perspective view of the articulator with upper and lower blocks ready to slide in place.

In FIG. 4, pins 4 have a tapered shaft 68 and a knurled head 50 which are placed in selected holes 26 in lower pin block 3 and upper pin block 53. The knurled head firmly secures the pins within the stone casts. The pin blocks are manufactured with close fitting elastomeric plugs 70 in every hole. The plugs in the position in which the pins are to be placed are easily pushed out. The plugged holes prevent the stone casting material from migrating and locking into unused holes and possibly fracturing the stone cast upon removal. A sheet of molded plugs can be manufactured and inserted in an articulator pin block in one operation. The sheet can be sheared away in a second manufacturing operation, leaving all the plugs in place. In an alternate embodiment of the invention, the holes are covered and protected by a thin sheet of polymer film or tape adhered to the pin block surface. The pins can be inserted in any desired through-hole by puncturing and displacing the thin sheet of polymer or tape over the desired hole. The end of the pin can have a sharpened annular bottom edge to cut the polymer sheet creating an access for the pin into the through-hole. Alternately, a sharp point on the end of the pin can aid in perforating the polymer film over the desired through-hole. A separate tool can punch through the polymer film to allow access to the through-hole.

FIG. 4 shows the placement of upper pin block 53 and lower pin block 3 within respective slide grooves 62 and 69 of articulator 60. The groove and pin block are equipped with suitable detent means to hold the pin blocks in place and indicate proper seating. Upper articulator frame 61 is connected to a rigid extension bar 63 and elastically flexible, angle bar 64 to hinge 65. Lower articulator frame 67 is connected with an elastically flexible angle bar 66 to the same hinge 65. The upper and lower frames of the articulator can be moved relative to each other to duplicate the complex motion of the human jaw. Forward and lateral motions that rely upon the elastically flexible bars 64 and 66 accomplish this task.

Upper forward stop 76 and lower forward stop 75 have respective mating and tracking surfaces 78 and 77 that hold both frames parallel in closure and guide the replication of the arc of motion of the jaw. These stops can be both removable and adjustable. FIG. 4 also features a removable set of rear stops 79 and 80 to maintain a parallel plane when constructing prosthetics for an edentulous ridge.

Figure 5:
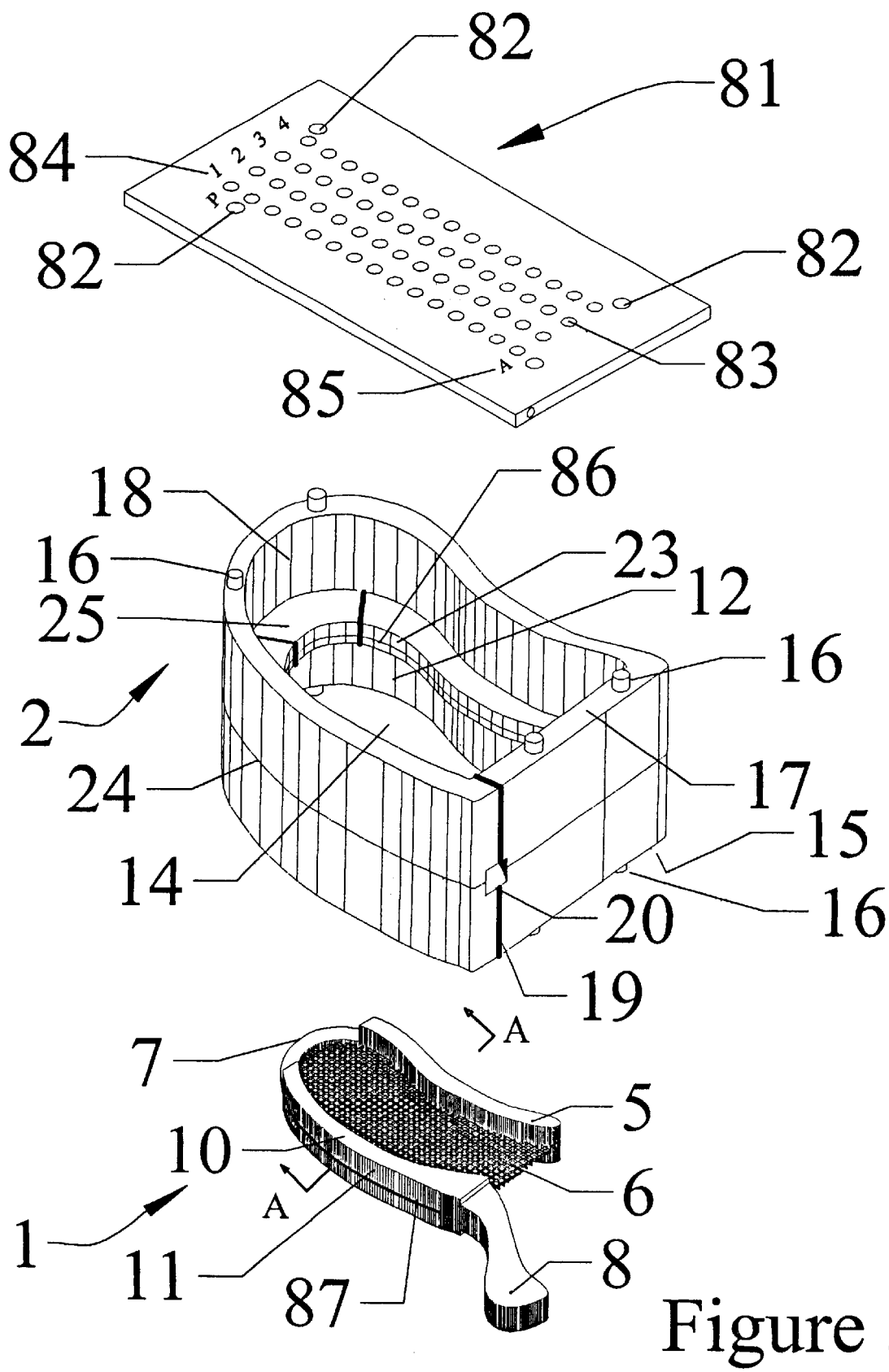
FIG. 5 is a perspective view of a pin location template.

FIG. 5 details a template 81 to aid in selection of the best pin positions. Alignment through-holes 82 over posts 16 allow the template to be accurately positioned upon the dam and triple tray assembly. The array of holes labeled 'A' through 'P' and '1' through '4' along orthogonal axes, as an example, let the dentist communicate the best pin placement to the technician. Similar markings on the pin block allow the correct holes for the pins to be chosen.

What is claimed is:

1. An apparatus for precise registration and articulation of upper and lower dental stone replicas comprised of a triple tray having a rigid frame and a thin porous membrane mounted on said frame in an occlusal plane;

a confining dam with upper and lower plaster stone casting recesses and an internal shelf conformable to a periphery of the triple tray frame, the confining dam having an upper surface parallel to the occlusal plane and lower surface parallel to the occlusal plane; said confining dam upper and lower surfaces having alignment posts;

a transparent, rigid polymer, upper articulator block with a multitude of evenly spaced tapered through-holes, each of the through-holes temporarily occluded with a locally removable barrier to prevent egress of plaster slurry;

a transparent, rigid polymer, lower articulator block with a multitude of evenly spaced tapered through-holes, each of the through-holes temporarily occluded with a locally removable barrier to prevent egress of plaster slurry;

said upper and lower articulator blocks having alignment holes mating with said alignment posts on the upper and lower surfaces of said confining dam;

a plurality of pins having a tapered base matching the tapered through-holes in said upper and lower articulator blocks, the pins having embedding heads capable of holding said pins within said stone replicas;

an articulator having an upper jaw connected to an upper arm with a flexing element, the flexing element connecting to a hinge, and a lower jaw connected to a lower arm with a flexing element connecting to said hinge, said flexing elements and said hinge exercising said upper and lower articulator jaws to mimic the motions of the human jaw;

said upper and lower articulator blocks having protruding ridges respectively sliding into upper and lower mating grooves in said upper and lower articulator jaws, in order to maintain plane parallel occlusal relationship between said upper and lower stone replicas replicated from said triple tray.

2. An apparatus as cited in claim 1 with a positive snap locking means between said upper articulator block and said upper articulator jaw groove.

3. An apparatus as cited in claim 1 with positive snap locking means between said lower articulator block and said lower articulator jaw groove.

4. An apparatus as cited in claim 1 having said confining dam comprised of at least one peripheral break and at least one hinged section and latch to allow said dam to open and close securely around said triple tray periphery.

5. An apparatus as in claim 1 having said confining dam comprised of at least two interlocking pieces.

6. An apparatus as cited in claim 1 having said internal shelf of said confining dam comprised of projections mating with matching depressions in the periphery of said triple tray frame to maintain said confining dam and said triple tray frame parallel to said occlusal plane.

7. An apparatus as cited in claim 1 in which said articulator blocks have identifying letters and numbers to uniquely locate said each through-hole.

8. An apparatus as cited in claim 1 further including a thin transparent template comprising alignment holes mating with said confining dam alignment posts, a plurality of through-holes, and identifying letters and numbers to locate proper placement of said pins.

9. An apparatus as cited in claim 1 in which said articulator upper and lower jaws have removable, adjustable frontal stops comprised of curved mating and tracking surfaces to mimic human jaw motion.

10. An apparatus as cited in claim 1 in which said articulator upper and lower jaws have removable, adjustable rear stops comprised of curved mating and tracking surfaces to mimic human jaw motion.

11. An apparatus as cited in claim 1 having said triple tray frame comprised of at least one peripheral recess mating with at least one projection on said confining dam internal shelf to maintain parallel registration.

12. An apparatus as cited in claim 1 having said triple tray frame comprised of at least one peripheral projection mating with at least one recess on said confining dam internal shelf to maintain parallel registration.

* * * * *